(12) United States Patent
Mercier et al.

(10) Patent No.: US 7,488,471 B2
(45) Date of Patent: Feb. 10, 2009

(54) TRANSPARENT OIL-IN-WATER EMULSION

(75) Inventors: Michel F. Mercier, Mountainside, NJ (US); Paul Thau, Berkeley Heights, NJ (US); John A. Chase, Bedminster, NJ (US)

(73) Assignee: MMP, Inc., South Plainfield, NJ (US)

( * ) Notice: Subject to any disclaimer, the term of this patent is extended or adjusted under 35 U.S.C. 154(b) by 317 days.

(21) Appl. No.: 10/282,821

(22) Filed: Oct. 28, 2002

(65) Prior Publication Data

US 2004/0081633 A1 Apr. 29, 2004

(51) Int. Cl.
*A61Q 5/00* (2006.01)
*A61Q 19/00* (2006.01)
(52) U.S. Cl. .................... 424/70.31; 424/401
(58) Field of Classification Search .............. None
See application file for complete search history.

(56) References Cited

U.S. PATENT DOCUMENTS

| | | | |
|---|---|---|---|
| 4,379,755 A * | 4/1983 | Yamada et al. ............. 516/73 |
| 4,526,780 A | 7/1985 | Marschner et al. |
| 4,784,844 A | 11/1988 | Thimineur |
| 4,814,165 A | 3/1989 | Berg et al. |
| 4,842,848 A | 6/1989 | Saita et al. |
| 4,983,377 A | 1/1991 | Murphy et al. |
| 4,983,418 A | 1/1991 | Murphy et al. |
| 5,250,289 A | 10/1993 | Boothroyd et al. |
| 5,290,555 A | 3/1994 | Guthauser et al. |
| 5,300,286 A | 4/1994 | Gee |
| 5,478,550 A | 12/1995 | Suzuki et al. |
| 5,599,533 A | 2/1997 | Stepniewski et al. |
| 5,620,682 A | 4/1997 | Fogel |
| 5,725,845 A | 3/1998 | Krog et al. |
| 5,746,945 A * | 5/1998 | Ryklin et al. ............. 516/23 |
| 5,750,096 A | 5/1998 | Guskey |
| 5,789,506 A | 8/1998 | Toribuchi et al. |
| 5,798,111 A | 8/1998 | Kanga et al. |
| 5,800,816 A | 9/1998 | Brieva et al. |
| 5,804,173 A | 9/1998 | Hutchins et al. |
| 5,830,447 A | 11/1998 | Hutchins et al. |
| 5,840,286 A | 11/1998 | Gardlik et al. |
| 5,863,525 A | 1/1999 | Angelone, Jr. et al. |
| 5,863,527 A | 1/1999 | Hutchins et al. |
| 5,863,546 A | 1/1999 | Swinehart |
| 5,876,702 A * | 3/1999 | Gers-Barlag et al. .......... 424/59 |
| 5,911,974 A | 6/1999 | Brieva et al. |
| 5,916,548 A | 6/1999 | Hutchins et al. |
| 5,922,311 A * | 7/1999 | Terren et al. ............. 424/70.12 |
| 5,972,359 A | 10/1999 | Sine et al. |
| 5,980,921 A | 11/1999 | Biedermann et al. |
| 5,985,298 A | 11/1999 | Brieva et al. |
| 5,997,890 A | 12/1999 | Sine et al. |
| 6,001,373 A | 12/1999 | Igo-Kemenes et al. |
| 6,001,377 A | 12/1999 | SaNogueira, Jr. et al. |
| 6,022,547 A | 2/2000 | Herb et al. |
| 6,045,782 A | 4/2000 | Krog et al. |
| 6,066,314 A | 5/2000 | Tang et al. |
| 6,103,250 A | 8/2000 | Brieva et al. |
| 6,120,778 A | 9/2000 | Simonnet |
| 6,171,581 B1 | 1/2001 | Joshi et al. |
| 6,171,601 B1 | 1/2001 | Gardlik et al. |
| 6,174,533 B1 | 1/2001 | SaNogueira, Jr. et al. |
| 6,183,766 B1 | 2/2001 | Sine et al. |
| 6,274,152 B1 | 8/2001 | Brieva et al. |
| 6,299,890 B1 | 10/2001 | Russ et al. |
| 6,333,053 B1 | 12/2001 | Simon |
| 6,355,260 B1 | 3/2002 | Tanaka et al. |
| 6,361,783 B2 | 3/2002 | Moaddel et al. |
| 6,365,141 B2 | 4/2002 | Nye et al. |
| 6,365,629 B1 | 4/2002 | Zofchak et al. |
| 6,379,682 B1 | 4/2002 | Tchinnis et al. |
| 6,419,909 B1 | 7/2002 | Lorant et al. |
| 6,616,917 B2 | 9/2003 | L'Orant et al. ............. 424/59 |
| 7,262,158 B1 * | 8/2007 | Lukenbach et al. ......... 510/122 |
| 2002/0172703 A1 | 11/2002 | L'Orant et al. ............. 424/401 |

FOREIGN PATENT DOCUMENTS

| | | |
|---|---|---|
| EP | 1097704 A1 | 5/2001 |
| FR | 2618351 A1 | 1/1989 |
| GB | 2 079 300 A | 1/1982 |

OTHER PUBLICATIONS

Goldemberg, "Silicones in Clear Emulsions," *Drug & Cosmetic Industry*, vol. 138, No. 2, pp. 34, 38, 40, 44 (Feb. 1986).

DiSapio, "New Approaches to Antiperspirant and Deodorant Formulation," *Household & Personal Products Industry*, pp. 43, 46, 50, 52 (Feb. 1986).

(Continued)

*Primary Examiner*—Jyothsna A Venkat
(74) *Attorney, Agent, or Firm*—Louis C. Paul

(57) ABSTRACT

The present invention relates to transparent or clear emulsions for cosmetic or pharmaceutical use. The transparent emulsions of the present invention comprise an oil phase, containing at least one lipophilic solvent; an aqueous phase; and an emulsifying system containing at least one non-ethoxylated fatty acid ester emulsifier having a hydrophilic-lipophilic balance ("HLB") from about 11 to about 16. Preferred non-ethoxylated fatty acid ester emulsifiers are sucrose esters, in particular sucrose palmitate and sucrose laurate.

16 Claims, No Drawings

OTHER PUBLICATIONS

Kahlweit, "Microemulsions" *Science* vol. 240, pp. 617-621 (Apr. 1988).

Deroni, "Microemulsions: A New Vehicle to Enhance the Efficacy of Active Ingredients in Cosmetics" from the 16$^{th}$ Congress of the IFSCC, The New York Hilton, New York, NY, vol. 2, pp. 62-67 (Oct. 1993).

Gallagher, "Microemulsion Gels: A Formulator's Guide," *Household & Personal Products Industry* pp. 58-64 (Feb. 1993).

Dow Corning, "Silicone Formulation Aids" (1995) (16 pages).

Rosen, "Silicone Innovation for Hair," *Global Cosmetic Industry*, vol. 170, No. 5, pp. 37-39 (May 2002).

Sisterna, "Sisterna Sucrose Esters: A Novel Range of Multifunctional Raw Materials" (140 pages).

Nelen, "Sisterna Sucrose Esters: The Route to Mildness,"from the HBA Global Exposition, Jacob Javits Convention Center, New York, NY (Oct. 14, 2002) (1 page).

Sisterna, "The Route to Mildness in Personal Care" from the HBA Global Exposition, Jacob Javits Convention Center, New York, NY (Oct. 14, 2002) (27 pages).

Database WPI Week 197430, Derwent Publications Ltd., London GB AN 1974-54387V; JP 49 009506 A.

\* cited by examiner

TRANSPARENT OIL-IN-WATER EMULSION

BACKGROUND OF THE INVENTION

Emulsions are formed from at least two liquid phases, typically oil and water, that are immiscible in each other. In an oil-in-water emulsion, for example, the oil phase is comprised of ingredients which are substantially insoluble in water. In this type of emulsion, the oil phase is composed of droplets that are finely dispersed in the water phase. It is therefore referred to as the inner or discontinuous phase, while the water phase is referred to as the outer or continuous phase. Conversely, in a water-in-oil emulsion, the water phase is finely dispersed in the oil phase and is referred to as the inner, discontinuous, phase, while the oil phase is the outer, continuous phase. Emulsions are inherently unstable and tend to separate into their constituent phases. Emulsions must therefore include emulsifiers which help create and maintain the uniform fine dispersion of the inner phase in the outer phase, and retard or prevent coalescence of the droplets and eventual separation of the emulsion into its constituent phases.

Emulsions—both water-in-oil and oil-in-water—are typically opaque (i.e., white or pale yellow in color). Transparent emulsion systems were described, in theory, as early as the 1940s. In those systems, in order to achieve transparency, the refractive indexes of the oil and water phases had to be matched prior to formation of the emulsion. See, e.g., Clayton, *Theory of Emulsions*, page 153 ($4^{th}$ Edition, 1943). Although they had been described in the 1940's, transparent emulsion systems of this type did not become commercially available until much later.

Transparent emulsions first became commercially available in the early 1960s. However, these emulsions did not achieve their transparency by matching refractive indexes. Rather, a transparent appearance was achieved by making the size of the dispersed droplets small enough (i.e., less than about 0.08 microns) so as to be unresolvable by visible light. Such emulsions are known as microemulsions. See, e.g., Gallagher, "Microemulsion Gels: A Formulator's Guide," *Happi* (February 1993). Microemulsions typically required a high content (i.e., 15-20%) of high hydrophilic-lipophilic balance ("HLB") non-ionic ethoxylated emulsifiers. Illustrative are Score™ and Clean and Groom™ hair dressings. See, e.g., U.S. Pat. No. 3,101,300. Because non-ionic ethoxylated emulsifiers are defatting and irritating to the skin when used at high levels, products containing them were viewed as unacceptable for topical application to the skin for an extended period of time. At least one previous attempt to formulate a clear microemulsion gel without the use of ethoxylated emulsifiers was unsuccessful. Gallagher described such an ethoxylated emulsifier-free microemulsion gel as not stable, having a very high set point, becoming clouded upon aging. Gallagher, supra.

By the early 1980s—with the availability of cyclomethicone and the introduction of specialty water-in-silicone emulsifiers (e.g. dimethicone copolyols) as raw materials—the development of transparent water-in-oil emulsions that were not microemulsions and that achieved their transparency by matching the refractive indexes of the oil and water phase became commercially possible. See, e.g., Dow Corning, "Using Silicone Formulation Aids to Formulate Cosmetic Systems: Quick Start Guide" (1995). Such transparent water-in-oil emulsions had several drawbacks. For example, they have the drawbacks typically associated with water-in-oil emulsions in general, such as delayed bioavailability of water-soluble active ingredients. Because such active ingredients are in the inner phase they can only become bioavailable after the emulsion breaks down. In addition, it is difficult to make refractive index adjustments at the end of processing. Therefore, in order to achieve transparency, the refractive indexes of the oil and water phases of these transparent water-in-oil emulsions had to be matched before combining the two phases.

Transparent oil-in-water emulsions overcome the above limitations. First, they have the advantageous characteristics typical of oil-in-water emulsions. Thus, for example, water-soluble active ingredients can be easily added to the aqueous phase and are bioavailable at, or shortly after, application. In addition the refractive index of the aqueous phase can be readily adjusted (e.g., by adding water to adjust the refractive index downward, or by adding glycerin or propylene glycol to adjust the refractive index upward) after the emulsion has been formed to match the refractive index of the oil phase. It is therefore not necessary to perfectly match the refractive indexes of the two phases before formation of the emulsion.

While some transparent oil-in-water emulsions have been described in the prior art, such emulsions generally contain ethoxylated emulsifiers and have a tendency to dry the skin. Furthermore, they generally require more vigorous mixing and are more viscous so that they tend to trap bubbles, which are difficult to remove and which negatively affect the clarity of the final product. Thus, there is a need for transparent oil-in-water emulsions which are not only milder to the skin, but also easier to process.

SUMMARY OF THE INVENTION

The invention is a novel transparent or clear oil-in-water emulsion which comprises an oil phase containing at least one lipophilic solvent; an aqueous phase; and an emulsifying system containing at least one non-ethoxylated fatty acid ester having an HLB from about 11 to about 16. The refractive indexes of the aqueous and oil phases of the emulsion are matched so that the resulting emulsion is essentially transparent or clear. The refractive index of the aqueous phase is about ±0.003 to about ±0.007 of that of the oil phase, preferably about or less than ±0.005. Optionally, a polymeric additive may be incorporated into the aqueous phase of the emulsion to create an emulsion gel of varying viscosities depending on the amount and type of polymer used.

DETAILED DESCRIPTION OF INVENTION

The transparent oil-in-water emulsion of the present invention is suitable for application to skin or hair. The novel transparent or clear oil-in-water emulsion comprises an oil phase containing at least one lipophilic solvent; an aqueous phase; and an emulsifying system containing at least one non-ethoxylated fatty acid ester having an HLB from about 11 to about 16. The refractive indexes of the aqueous and oil phases of the emulsion are matched so that the resulting emulsion is essentially transparent or clear. The refractive index of the aqueous phase is about ±0.003 to about ±0.007 of that of the oil phase, preferably about or less than ±0.005. Optionally, a polymeric additive may be incorporated into the aqueous phase of the emulsion to create an emulsion gel of varying viscosities depending on the amount and type of polymer used.

The oil-in-water emulsions of the present invention are exceptionally mild. This is not only because the emulsifiers used in the present invention are exceptionally mild and considerably less irritating to the skin and eyes than ethoxylated emulsifiers, but also because surprisingly the level necessary to stabilize the emulsions (and thus the total level of total emulsifier present) has been found to be very low. Indeed, surprisingly sucrose esters alone can stabilize the emulsions of the invention. The water-in-oil emulsions of the present invention surprisingly have also been found to have skin moisturizing properties.

In addition to their mild and hydrating characteristics, the emulsions of the present invention are also more conveniently processed. In order to achieve transparency in an emulsion, it is important that air bubbles be eliminated or essentially minimized from the emulsion. Prior art emulsions, in particular those containing ethoxylated emulsifiers, required high shear mixing which tends to entrap small bubbles. Since removal of smaller bubbles is difficult, those bubbles often remain in the final products, thereby decreasing clarity and transparency. In contrast, it has been surprisingly found that transparent oil-in-water emulsions of the present invention may be formed by medium energy loop mixing. Bubbles produced during this lower energy process tend to be bigger and rise to the surface of the emulsion (where they burst), thus resulting in an essentially bubble-free emulsion. Furthermore, since a stable emulsion according to the present invention can be formed with low levels of sucrose esters, the resulting base emulsion is relatively more flowable than prior art emulsions which required a larger concentration of surfactant, and thus tend to be more viscous. Whereas bubbles become entrapped in the more viscous prior art base emulsions, the more flowable emulsions of the present invention allow bubbles to rise and dissipate, producing an aesthetically acceptable transparent base emulsion. The increased flowability of the emulsions of the present invention is also advantageous because the viscosity and consistency of the emulsion may be adjusted within a relatively wide range after formation of the emulsion by the addition of polymeric additives in the quantity and type necessary to achieve the desired characteristics. Furthermore, this is accomplished on an essentially bubble-free base emulsion. In contrast, the addition of polymeric thickeners to prior art emulsions tends to further entrap smaller bubbles already present.

The oil phase of the present invention comprises at least one lipophilic solvent and preferably other lipophilic cosmetic or pharmaceutically useful ingredients known to those of ordinary skill in the art. Preferably the lipophilic solvent is selected from the group consisting of volatile silicone fluids, non-volatile silicone fluids, high molecular weight silicone polymers in the range from about 60,000 centistokes to about 1,000,000 centistokes, liquid fatty alcohols from 16 to 22 carbon atoms per molecule, volatile hydrocarbon fluids and vegetable oils. Preferred volatile silicone fluids which can be used in the oil phase of the present invention include cyclomethicone (cyclopentasiloxane, cyclohexasiloxane, cyclotetrasiloxane) and dimethicone (0.65 centistokes). A preferred volatile hydrocarbon fluid usable in the present invention is isododecane, sold under the tradename Permethyl 99A, by Presperse Inc., Piscataway, N.J. The oil phase may further comprise a lipophilic co-solvent selected from the group consisting of fatty acid esters, liquid branched chain fatty alcohols from 16 to 20 carbon atoms in length, and triglycerides. A preferred triglyceride is caprylic/capric triglyceride. To improve feel, dimethicone/vinyl dimethicone cross polymer may be added to the oil phase. The oil phase comprises from about 30% to about 70% by weight of the emulsion, preferably from about 40% to about 50%. In order to aid in matching refractive indexes of the aqueous and oil phases, the oil phase may include index adjusting agents known to those of ordinary skill in the art such as halogenated solvents.

The aqueous phase of the present invention comprises water and preferably other water-soluble cosmetically or pharmaceutically useful ingredients known to those of ordinary skill in the art. In order to aid in matching the refractive indexes of the aqueous and oil phases, the aqueous preferably includes one or more polyols selected from the group consisting of glycerin, polyethylene glycol, propylene glycol, polypropylene glycol, 1,3 butylene glycol, methylpropanediol, hexylene glycol and sorbitol. Preferably the polyol has a molecular weight from about 75 to about 10,000 daltons, more preferably from about 200 to about 5000 daltons, and most preferably from about 300 to about 1000 daltons. A preferred polyol for use in the present invention is polyethylene glycol 400, sold under the tradename Carbowax PEG 400 by Union Carbide, Houston, Tex., alone or in combination with glycerin. Preferably, the polyol is present in an amount of from about 10% to about 35% of the total composition, more preferably from about 15% to about 30% of the total composition, and most preferably it makes up from about 18% to about 25% of the total composition. Alternatively to the polyol, the aqueous phase of the emulsion may contain polysaccharides or other agents known to those of ordinary skill in the art to be useful in adjusting the refractive index of the aqueous phase.

The emulsifying system includes at least one non-ethoxylated fatty acid ester emulsifier having an HLB from about 11 to about 16, preferably from about 13 to about 16. Preferably the emulsifier is a sucrose ester. More preferably the sucrose ester emulsifier is selected from the group consisting of sucrose laurate, sucrose stearate, sucrose palmitate, sucrose oleate, sucrose myristate, sucrose cocoate and sucrose isostearate, or a combination thereof. Most preferably the non-ethoxylated emulsifier is a sucrose laurate or a sucrose palmitate. Preferably the percentage of the non-ethoxylated fatty acid ester is less than 5% by weight of the total composition, more preferably less than 3% by weight of the total composition, and most preferably less than 1.5%. When the non-ethoxylated fatty acid ester is a sucrose ester, the preferred range is from about 0.5 to 5% by weight of the total composition, and more preferably from about 1 to about 2.5% by weight of the total composition, and most preferably less than 1.5% of the total composition.

Optionally, a polymeric additive may be incorporated into the aqueous phase of the emulsion in order to achieve a desired viscosity or gel consistency. The polymeric additive is a water soluble polymer selected from the group consisting of sclerotium gum, xanthan gum, sodium alginate, carbomer, cellulose ethers and acrylate polymers. Sclerotium gum is sold under the tradename Clearogel CS11D by MMP, Inc., South Plainfield, N.J. Acrylate polymers usable in the present invention include: steareth-20 methylacrylate copolymer, sold under the tradename Aculyn 22 by Rohm & Haas Company, Philadelphia, Pa.; Pemulen TR-1 and TR-2 (C10-C30 alkyl acrylate crosspolymer), both sold by Goodrich Specialty Chemicals, Cleveland, Ohio; and Hypan QT1000 and SA100H, both acrylonitrogen copolymers, sold by Lipo Chemicals, Inc., Patterson, N.J. Preferred polymers for use in the present invention are Clearogel CS11D and Aculyn 22. Depending upon the viscosity to be achieved, the amount of polymeric additive can range from about 0.1% to about 2.5% by weight of the total composition, preferably 0.5 % to 0.75 % by weight of the total composition. In general, the greater the amount of the polymeric additive, the greater the viscosity.

The present invention can be utilized in a wide range of cosmetic and pharmaceutical products, including, but not limited to, transparent deodorant gels, transparent skin and eye moisturizing gels, transparent hair conditioner and glosser gels, transparent autobronzer gels, transparent sunscreen gels, transparent skin tightening gels and other transparent dermatologic vehicles for delivering pharmaceutically active ingredients (e.g., ascorbic acid and retinol).

In order to produce the desired products, the basic components of the invention as described above may be combined with other cosmetic and pharmaceutical ingredients which are well known to cosmetic and pharmaceutical chemists. Examples of such additional components include, but are not limited to, antiseborrheic agents, anti-acne agents, antioxidants, skin lightening agents, depigmenting agents, anti-wrinkle agents, vitamins, sunscreen agents, self-tanning agents, topical analgesics, anti-inflammatory agents, antipruritic agents, deodorants, as well as purely cosmetic ingredients, such as pigments, water soluble emollients, humectants, stabilizers and fragrances. Sunscreen agents which are most suitable for use in the present invention include octyl methoxycinnamate, octyl salicylate and avobenzone.

The transparent oil-in-water gel emulsion of the present invention is prepared according to principles and techniques generally known to those skilled in the cosmetic and pharmaceutical arts. As described below, a base emulsion comprising the oil and water phases and non-ethoxylated fatty acid ester emulsifier is prepared. A polymeric thickener is optionally added to the base emulsion when increased viscosity is desired. Finally, refractive indexes of the oil and water phases are matched. More particularly, ingredients which are miscible or soluble in the water phase are combined with the non-ethoxylated fatty acid ester emulsifier using a loop blade mixer at medium speed (i.e., from about 200 to about 250 rotations per minute) in a main vessel. Air bubbles, if any, are removed from the aqueous phase by slow mixing with a loop blade mixer (i.e., from about 60 to about 100 rotations per minute). Oil phase ingredients are combined in a separate vessel. After the refractive indexes of the oil and water phases are matched to one another using the polyols described above or other techniques and materials known to those of ordinary skill in the art, the oil phase is gradually added to the main vessel. The two phases are combined and emulsified by gradually increasing the speed of the loop mixer from slow to medium as described above. Next, polymeric thickeners are added. Lastly, final adjustments to match the refractive indexes are made (e.g., by adding water to adjust the refractive index downward, or by adding glycerin or propylene glycol to adjust the refractive index upward).

The invention is further illustrated by the following examples, which are intended to illustrate and not limit the invention.

EXAMPLE 1

Transparent Deodorant Gel

|  |  | % w/w |
|---|---|---|
| Phase A | Deionized water | 15.50 |
|  | Disodium ethylenediamine-tetraacetate (EDTA) | 0.10 |
|  | Glycerin | 12.00 |
|  | Polyethylene glycol (PEG-8) | 12.00 |
|  | Sucrose laurate (38% Sol.) | 4.00 |
| Phase B | Caprylic/Capric Triglyceride | 15.95 |
|  | Masking Fragrance | 0.30 |
|  | Cyclopentasiloxane | 35.00 |
| Phase C | Aculyn 22 | 2.00 |
|  | Water | 2.00 |
| Phase D | Sodium hydroxide (18% Sol.) | 1.15 |

The transparent deodorant gel of Example 1 was made according to the following procedure: The non-ethoxylated fatty acid ester emulsifier (i.e., sucrose laurate) and the remaining aqueous phase ingredients (i.e., deionized water, disodium EDTA, glycerin and PEG-8) were combined in a main mixing vessel with a loop blade mixer at medium speed (i.e., from about 200 to about 250 rpm). When the aqueous phase ingredients were fully combined, air bubbles were removed by slow mixing with a loop blade mixer (i.e., from about 60 to about 100 rpm), and the refractive index of Phase A was measured. Next, the oil phase ingredients (Phase B) were combined with a stirrer. Since the Phase B ingredients are easily miscible in one another, mechanical mixing (e.g., loop blade mixing) was not required. The refractive index of aqueous Phase A was measured and matched to within 0.005 of that of oil Phase B. Phase B was then gradually added to the main vessel containing Phase A; the two phases were combined using a loop blade mixer at medium speed creating a base emulsion. Next, the polymeric thickener of Phase C (i.e., Aculyn 22) was added to the base emulsion. Sodium hydroxide (Phase D) was then added to the emulsion of Phases A, B and C thereby raising the pH of the base emulsion, activating the Aculyn 22 to form a polymeric matrix, and thickening the emulsion to the desired viscosity. Final adjustments were made to match the refractive index of the water phase to that of the oil phase by adding water or glycerin.

The deodorant gel of Example 1 was transparent and had a viscosity 49,500 centipoise with a pH of 7.0. Viscosity was measured using a Brookfield viscometer with an LV4 spindle at 12 rpm; pH was measured using a standard pH meter. This emulsion was stable at 45° C. for more than two months, at room temperature for more than six months, and after three freeze/thaw cycles.

EXAMPLE 2

Transparent Hair Gel

|  |  | % w/w |
|---|---|---|
| Phase A | Deionized Water | 17.30 |
|  | Disodium EDTA | 0.10 |
|  | Carbomer | 0.50 |
|  | Sucrose laurate (38% Sol.) | 4.00 |
|  | Hydrolyzed wheat protein | 1.00 |
|  | Glycerin | 12.00 |
|  | PEG-8 | 12.00 |
| Phase B | Cyclopentasiloxane | 35.00 |
|  | Phenyl trimethicone | 5.00 |
|  | Caprylic/Capric triglyceride | 11.45 |
|  | Masking fragrance | 0.30 |
| Phase C | Sodium hydroxide (18% Sol.) | 1.35 |

The transparent hair gel of Example 2 was made as described below. The aqueous phase ingredients (Phase A) were combined in the following order: Carbomer was fully dispersed in the mixture of deionized water and disodium EDTA in a main mixing vessel with a loop blade mixer at medium speed (i.e., from about 200 to about 250 rpm). Next, the non-ethoxylated fatty acid ester emulsifier (i.e., sucrose laurate) was added, followed by the hydrolized wheat protein, then PEG-8 and, finally, glycerin. When the aqueous phase ingredients were fully combined, air bubbles were removed by slow mixing with the loop blade mixer (i.e., from about 60 to about 100 rpm), and the refractive index of Phase A was measured. Next, the oil phase ingredients (Phase B) were combined with a stirrer. Since the Phase B ingredients are easily miscible in one another, mechanical mixing (e.g., loop blade mixer) was not required. The refractive index of aqueous Phase A was measured and matched to within 0.005 of that of oil Phase B. Phase B was then gradually added to the main vessel containing Phase A and the two phases were combined using a loop blade mixer at medium speed. Finally, sodium hydroxide (Phase C) was added to raise the pH of the base emulsion, thereby activating the carbomer to form a polymeric matrix and thickening the emulsion to the desired viscosity. Final adjustments were made to match the refractive index of the water phase to that of the oil phases by adding water or glycerin.

The hair gel of Example 2 was transparent and had a viscosity of 42,000 centipoise with a pH of 6.8. Viscosity and pH were measured as in Example 1. This emulsion was stable at 40° C. for more than two months, at room temperature for more than six months, and after three freeze/thaw cycles.

EXAMPLE 3

| | Transparent Autobronzer | |
|---|---|---|
| | | % w/w |
| Phase A | Deionized water | 27.50 |
| | Disodium EDTA | 0.10 |
| | Glycerin | 5.00 |
| | PEG-8 | 10.00 |
| | Dihydroxyacetone | 5.00 |
| | Sucrose laurate (38% Sol.) | 4.00 |
| Phase B | Cyclopentasiloxane | 42.50 |
| | Fragrance | 0.30 |
| Phase C | Glycerin | 5.00 |
| | Sodium alginate | 0.60 |

The transparent autobronzer gel of Example 3 was made according to the following procedure: The aqueous phase of the emulsion was prepared by combining the non-ethoxylated fatty acid ester emulsifier (i.e., sucrose laurate) with deionized water, disodium EDTA, PEG-8 and dihydroxyacetone in a main mixing vessel with a loop blade mixer at medium speed (i.e., from about 200 to about 250 rpm). When the aqueous phase ingredients were fully combined, air bubbles were removed by slow mixing with the loop blade mixer (i.e., from about 60 to about 100 rpm). The refractive indexes of Phases A and B were matched to within 0.005 of one another. Phase B was then gradually added to the main vessel; mixing speed was gradually increased from slow to medium according to the above-described ranges. Glycerin and sodium alginate were combined into a slurry in a separate vessel. That slurry was then gradually added to the main vessel and medium speed mixing was continued for 30 minutes. Final adjustments were made to match the refractive index of the water phase to that of the oil phase by adding water or glycerin.

The autobronzer gel of Example 3 was transparent and had a viscosity of 17,000 centipoise with a pH of 5.0. Viscosity and pH were measured as in Example 1. This emulsion was stable at 40° C. for more than two months, at room temperature for more than six months, and after three freeze/thaw cycles.

EXAMPLE 4

| | Transparent Eye Gel | |
|---|---|---|
| | | % w/w |
| Phase A | Deionized water | 27.50 |
| | Disodium EDTA | 0.10 |
| | Sucrose Palmitate | 2.00 |
| | Glycerin | 7.00 |
| | PEG-8 | 13.00 |
| Phase B | Cyclomethicone | 32.95 |
| | Caprylic/Capric Triglyceride | 12.00 |
| | Fragrance | 0.30 |
| Phase C | Glycerin | 5.00 |
| | Clearogel CS11D | 0.15 |

The transparent eye gel of Example 4 was made according to the following procedure: A trial aqueous phase system was prepared by combining at 55° C. the non-ethoxylated fatty acid ester emulsifier (i.e., sucrose palmitate) with deionized water, disodium EDTA, glycerin and PEG-8 of Phase A with the glycerin of Phase C in a main mixing vessel with a loop blade mixer at medium speed (i.e., from about 200 to about 250 rpm). When the trial aqueous system ingredients were fully combined, air bubbles were removed by slow mixing with the loop blade mixer (i.e., from about 60 to about 100 rpm). The trial aqueous system was allowed to cool to about 40° C. at which time its refractive index was measured. Next, the oil Phase B of the emulsion was prepared by combining cyclomethicone, caprylic/capric triglyceride and fragrance in a side mixing vessel. Since the Phase B ingredients are easily miscible in one another, mechanical mixing (e.g., loop blade mixer) was not required. The refractive index of the trial aqueous phase system was then matched to within 0.005 of that of oil Phase B by adding glycerin or water to the trial aqueous phase.

Aqueous Phase A (i.e., without the glycerin of Phase C) was then prepared by combining the ingredients listed in the table above in a main mixing vessel with an amount of water or glycerin determined to be necessary to match the refractive index of the trial aqueous phase system to within 0.005 of that of oil Phase B. Phase B was then gradually added to the main mixing vessel; mixing speed was gradually increased from slow to medium according to the above-described ranges. Next, the sclerotium gum polymeric additive (i.e., Clearogel CS11D) and glycerin of Phase C were combined into a slurry in a separate vessel. That slurry was then gradually added to the main vessel and medium speed mixing was continued for 30 minutes at 35-40° C. Final adjustments were made to match the refractive index of the aqueous phase to 0.005 of that of oil phase.

The eye gel of Example 4 was transparent and had a viscosity of 16,000 centipoise with a pH of 6.45. Viscosity and pH were measured as in Example 1.

We claim:
1. A transparent oil-in-water gel emulsion composition for application to skin or hair comprising:
   (a) an oil phase, containing at least one lipophilic solvent;
   (b) an aqueous phase, containing at least one polyol;
   (c) at least one sucrose ester emulsifier having an HLB from about 11 to about 16 at a concentration of less than

5% by weight of the total composition; wherein the at least one sucrose ester emulsifier is selected from the group consisting of sucrose laurate, sucrose stearate, sucrose palmitate, sucrose oleate, sucrose myristate, sucrose cocoate, and sucrose isostearate; and (d) a polymeric thickener wherein the polymeric thickener is selected from the group consisting of sclerotium gum, xanthan gum, sodium alginate, Carbomer, cellulose ethers, steareth-20 methylacrylate copolymer and C10-C30 alkyl acrylate crosspolymer wherein the refractive index of the aqueous phase is about or less than +/−0.005 of that of the oil phase.

2. A composition according to claim 1 wherein the lipophilic solvent of the oil phase is selected from the group consisting of volatile silicone fluids, non-volatile silicone fluids, high molecular weight silicone polymers in the viscosity range of from about 60,000 centistokes to about 1,000,000 centistokes, liquid fatty alcohols from 16 to 22 carbon atoms per molecule, volatile hydrocarbon fluids, esters and vegetable oils.

3. A composition according to claim 2 wherein the lipophilic solvent of the oil phase is a volatile silicone fluid.

4. A composition according to claim 3 wherein the volatile silicone fluid is selected from the group consisting of cyclomethicone (cyclopentasiloxane, cyclohexasiloxane, cyclotetrasiloxane) and dimethicone (0.65 centistokes).

5. A composition according to claim 2 wherein the lipophilic solvent of the oil phase is a volatile hydrocarbon fluid.

6. A composition according to claim 5 wherein the volatile hydrocarbon fluid is isododecane.

7. A composition according to claim 1 wherein the lipophilic solvent of the oil phase further comprises a lipophilic co-solvent selected from the group consisting of fatty acid esters and triglycerides.

8. A composition according to claim 1 wherein the polyol of the aqueous phase is selected from the group consisting of glycerin, polyethylene glycol, propylene glycol, polypropylene glycol, 1,3 butylene glycol, methylpropanediol, hexylene glycol and sorbitol.

9. A composition according to claim 1 wherein the molecular weight of the polyol is from about 300 to about 1,000 daltons.

10. A composition according to claim 1 wherein the polyol is polyethylene glycol 400.

11. A composition according to claim 1 wherein the at least one sucrose ester emulsifier is present at a concentration of less than about 3% by weight of the total composition.

12. A composition according to claim 11 wherein the at least one sucrose ester is a sucrose laurate.

13. A composition according to claim 11 wherein the at least one sucrose ester is a sucrose palmitate.

14. composition according to claim 1 wherein the at least one sucrose ester emulsifier is present at a concentration of less than about 1.5% by weight of the total composition.

15. A composition according to claim 14 wherein the at least one sucrose ester is a sucrose laurate.

16. A composition according to claim 14 wherein the at least one sucrose ester is a sucrose palmitate.

* * * * *